United States Patent
Davis

(10) Patent No.: US 7,112,223 B2
(45) Date of Patent: Sep. 26, 2006

(54) PSEUDO ARTHROSIS DEVICE

(75) Inventor: Reginald Davis, Cockeysville, MD (US)

(73) Assignee: Abbott Spine Inc., Austin, TX (US)

( * ) Notice: Subject to any disclaimer, the term of this patent is extended or adjusted under 35 U.S.C. 154(b) by 0 days.

(21) Appl. No.: 10/331,191

(22) Filed: Dec. 27, 2002

(65) Prior Publication Data

US 2003/0229397 A1    Dec. 11, 2003

Related U.S. Application Data

(63) Continuation-in-part of application No. 10/035,052, filed on Dec. 28, 2001, now Pat. No. 6,736,850.

(51) Int. Cl.
*A61F 2/44* (2006.01)

(52) U.S. Cl. .................. 623/17.16; 623/17.13

(58) Field of Classification Search ... 623/17.11–17.16
See application file for complete search history.

(56) References Cited

U.S. PATENT DOCUMENTS

| | | |
|---|---|---|
| 3,867,728 A | 2/1975 | Stubstad et al. |
| 4,309,777 A | 1/1982 | Patil |
| 4,349,921 A | 9/1982 | Kuntz |
| 4,759,766 A | 7/1988 | Buettner-Janz et al. |
| 4,759,769 A | 7/1988 | Hedman et al. |
| 4,772,287 A | 9/1988 | Ray et al. |
| 4,863,477 A | 9/1989 | Monson |
| 4,911,718 A | 3/1990 | Lee et al. |
| 4,932,975 A | 6/1990 | Main et al. |
| 4,946,378 A | 8/1990 | Hirayama et al. |
| 5,047,055 A | 9/1991 | Bao et al. |
| 5,071,437 A | 12/1991 | Steffee |
| 5,108,438 A | 4/1992 | Stone |
| 5,123,926 A | 6/1992 | Pisharodi |
| 5,171,281 A | 12/1992 | Parsons et al. |
| 5,192,326 A | 3/1993 | Bao et al. |
| 5,246,458 A | 9/1993 | Graham |
| 5,258,031 A | 11/1993 | Salib et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner |

(Continued)

FOREIGN PATENT DOCUMENTS

FR    2799638    4/2001

(Continued)

OTHER PUBLICATIONS

International Search Report, Application No. PCT/US02/41425, mailed May 23, 2003.

*Primary Examiner*—Bruce Snow
*Assistant Examiner*—Cheryl Miller
(74) *Attorney, Agent, or Firm*—Beth A. Vrioni

(57) ABSTRACT

A pseudo arthrosis device may be placed in a disc space to provide support for adjacent vertebrae. The device may have an enclosure formed from a flexible, permeable material. A plurality of elongated members may be packed longitudinally in the enclosure. The elongated members may be compressible and/or flexible. In certain embodiments, elongated members may be solid rods and/or hollow tubes. A plurality of spaced-apart perforations may be formed in solid and hollow elongated members. The enclosure may be placed in an intervertebral space between the adjacent vertebrae such that the elongated members are disposed longitudinally between the adjacent vertebrae. The pseudo arthrosis device may include a tab designed to couple the enclosure to an adjacent vertebrae.

37 Claims, 4 Drawing Sheets

U.S. PATENT DOCUMENTS

| | | |
|---|---|---|
| 5,370,697 A | 12/1994 | Baumgartner |
| 5,401,269 A | 3/1995 | Buettner-Janz et al. |
| 5,425,773 A | 6/1995 | Boyd et al. |
| 5,458,642 A | 10/1995 | Beer et al. |
| 5,458,643 A | 10/1995 | Oka et al. |
| 5,514,180 A | 5/1996 | Heggeness et al. |
| 5,522,899 A | 6/1996 | Michelson |
| 5,534,028 A | 7/1996 | Bao et al. |
| 5,534,030 A | 7/1996 | Navarro et al. |
| 5,556,431 A | 9/1996 | Buettner-Janz |
| 5,562,738 A | 10/1996 | Boyd et al. |
| 5,674,294 A | 10/1997 | Bainville et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,702,450 A | 12/1997 | Bisserie |
| 5,755,797 A | 5/1998 | Baumgartner |
| 5,782,832 A | 7/1998 | Larsen et al. |
| 5,800,549 A | 9/1998 | Bao et al. |
| 5,824,093 A | 10/1998 | Ray et al. |
| 5,824,094 A | 10/1998 | Serhan et al. |
| 5,827,328 A | 10/1998 | Buttermann |
| 5,861,041 A | 1/1999 | Tienboon |
| 5,865,846 A | 2/1999 | Bryan et al. |
| 5,888,220 A | 3/1999 | Felt et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,961,554 A | 10/1999 | Janson et al. |
| 5,976,186 A | 11/1999 | Bao et al. |
| 5,984,967 A | 11/1999 | Zdeblick et al. |
| 6,001,130 A | 12/1999 | Bryan et al. |
| 6,019,792 A | 2/2000 | Cauthen |
| 6,022,376 A | 2/2000 | Assell et al. |
| 6,039,763 A | 3/2000 | Shelokov |
| 6,093,205 A | 7/2000 | McLeod et al. |
| 6,110,210 A | 8/2000 | Norton et al. |
| 6,113,637 A | 9/2000 | Gill et al. |
| 6,132,465 A | 10/2000 | Ray et al. |
| 6,136,031 A | 10/2000 | Middleton |
| 6,139,579 A | 10/2000 | Steffee et al. |
| 6,146,421 A | 11/2000 | Gordon et al. |
| 6,156,067 A | 12/2000 | Bryan et al. |
| 6,162,252 A | 12/2000 | Kuras et al. |
| 6,165,218 A | 12/2000 | Husson et al. |
| 6,179,874 B1 | 1/2001 | Cauthen |
| 6,187,048 B1 | 2/2001 | Milner et al. |
| 6,206,924 B1 | 3/2001 | Timm |
| 6,214,049 B1 | 4/2001 | Gayer et al. |
| 6,228,118 B1 | 5/2001 | Gordon |
| 6,296,664 B1 | 10/2001 | Middleton |
| 6,315,797 B1 | 11/2001 | Middleton |
| 6,348,071 B1 | 2/2002 | Steffee et al. |
| 6,419,704 B1 | 2/2002 | Manasas et al. |
| 6,368,350 B1 | 4/2002 | Erickson et al. |
| 6,371,990 B1 | 4/2002 | Ferree |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |
| 6,440,168 B1 | 8/2002 | Cauthen |
| 6,468,310 B1 * | 10/2002 | Ralph et al. ............ 623/17.13 |
| 6,478,822 B1 | 11/2002 | Leroux et al. |
| 6,482,234 B1 | 11/2002 | Weber et al. |
| 6,520,996 B1 | 2/2003 | Manasas et al. |
| 6,527,806 B1 * | 3/2003 | Ralph et al. ............ 623/17.16 |
| 6,576,017 B1 * | 6/2003 | Foley et al. ............ 623/17.16 |
| 6,638,310 B1 * | 10/2003 | Lin et al. ................ 623/17.11 |
| 2002/0128714 A1 | 9/2002 | Manasas et al. |
| 2002/0130112 A1 | 9/2002 | Manasas et al. |
| 2003/0018390 A1 | 1/2003 | Husson |
| 2003/0040800 A1 * | 2/2003 | Li et al. .................. 623/17.12 |

FOREIGN PATENT DOCUMENTS

| | | |
|---|---|---|
| WO | 00/04851 | 2/2000 |
| WO | 00/74606 | 12/2000 |

* cited by examiner

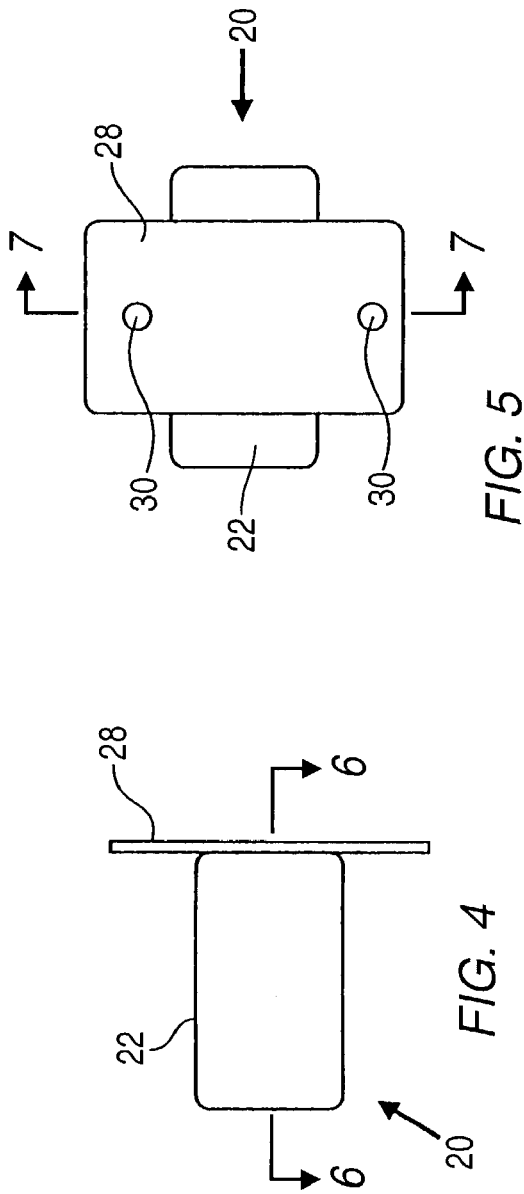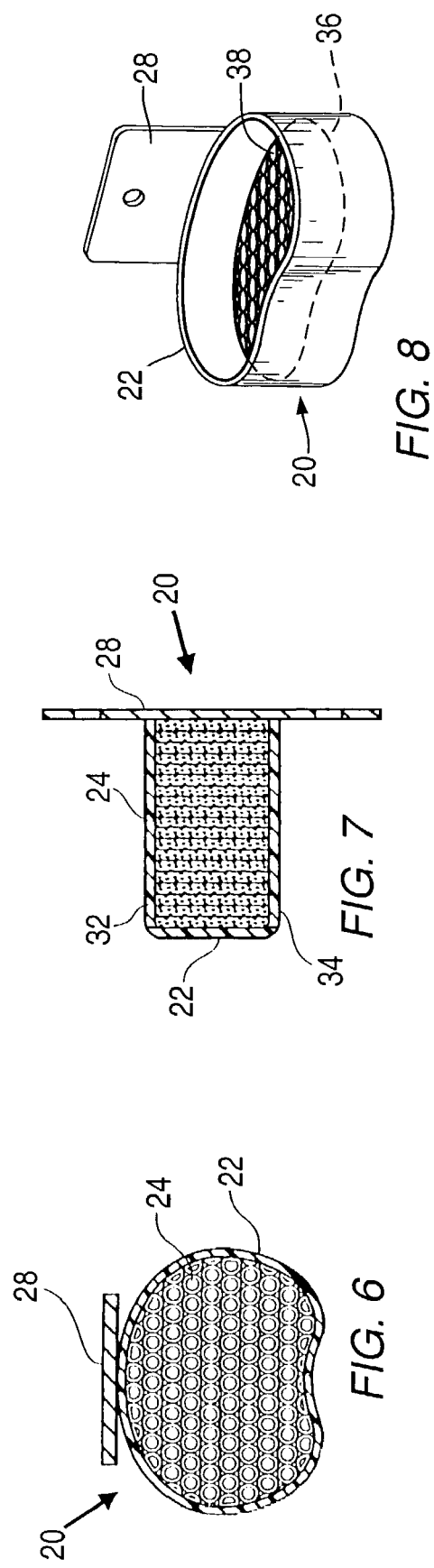

PSEUDO ARTHROSIS DEVICE

PRIORITY CLAIM

This application is continuation-in-part of U.S. patent application Ser. No. 10/035,052 entitled "PSEUDO ARTHROSIS DEVICE" filed on Dec. 28, 2001 now U.S. Pat. No. 6,736,850.

BACKGROUND

1. Field of Invention

The present invention generally relates to spinal implants for alleviating problems in human spines. More particularly, an embodiment of the invention relates to a device that replaces a damaged spinal disc and promotes fibrous ingrowth.

2. Description of Related Art

A spinal disc is a shock-absorbing structure located in a space between two adjacent vertebrae in a spine. A spinal disc may deteriorate due to trauma, disease, and/or aging. A deteriorated spinal disc may have diminished shock-absorbing capacity. A deteriorated disc may allow adjacent vertebrae to contact each other. Contact of adjacent vertebrae may result in wear and tear of the vertebrae. Wear and tear of the vertebrae may result in pain (e.g., neck and/or back pain).

Non-surgical treatments to reduce neck and/or back pain may include rest, heat, medication, physical therapy, and chiropractic manipulation. Non-surgical treatments may be ineffective for some patients.

Surgical treatment of a deteriorated spinal disc may include spinal fusion. A spinal fusion treatment may not be successful in some patients. When successful, spinal fusion treatments may result in stiffness and decreased mobility of the patient. Spinal fusion may cause stress on the spine at adjacent vertebral levels. The stress on the spine may create new spinal problems. New spinal problems may result in additional neck and/or back pain.

Surgical alternatives to spinal fusion may include spinal disc replacement. U.S. Pat. No. 3,567,728 to Stubstad et al.; U.S. Pat. No. 5,071,437 to Steffee; U.S. Pat. No. 5,320,644 to Baumgartner; U.S. Pat. No. 5,522,899 to Michelson; U.S. Pat. No. 5,961,554 to Janson et al.; U.S. Pat. No. 5,976,186 to Bao et al.; U.S. Pat. No. 6,162,252 to Kuras et al.; U.S. Pat. No. 6,206,924 to Timm; U.S. Pat. No. 6,214,049 to Gayer et al.; and U.S. Pat. No. 6,093,205 to McLeod et al., each of which is incorporated by reference as if fully set forth herein, describe devices for surgical treatment of deteriorated and/or damaged spinal discs.

SUMMARY

A pseudo arthrosis device may be a relatively inexpensive, simple device that is easily inserted into the spine to replace a damaged or degenerated disc. The pseudo arthrosis device may be compatible with the human body. In some embodiments, a pseudo arthrosis device may serve as a matrix or scaffold to support growth of body fibers in a patient. Growth of the patient's body fibers may incorporate the device into the patient. Incorporation of the device into the patient may allow the patient's body to repair itself.

In an embodiment, a pseudo arthrosis device may be placed in a disc space to provide support for adjacent vertebrae. The device may have an enclosure formed from a flexible, permeable material. A plurality of elongated members may be packed longitudinally in the enclosure. The elongated members may be compressible and/or flexible. In some embodiments, elongated members may be solid rods and/or hollow tubes. A plurality of spaced-apart perforations may be formed in solid and hollow elongated members. An enclosure may be placed in an intervertebral space between adjacent vertebrae such that the elongated members are disposed longitudinally between the adjacent vertebrae. The pseudo arthrosis device may include a tab designed to couple the enclosure to an adjacent vertebra.

A pseudo arthrosis device may be used to replace a damaged spinal disc. A method of replacing a damaged spinal disc may include removing a damaged spinal disc to form a disc space between two adjacent vertebrae in a patient's spinal column. An enclosure of a pseudo arthrosis device may be packed with a plurality of elongated members. A tab may be coupled to the enclosure. The pseudo arthrosis device may be placed in the disc space between the adjacent vertebrae. The tab may be coupled to one of the adjacent vertebrae to secure the enclosure between the adjacent vertebrae. The plurality of elongated members may be disposed longitudinally between the adjacent vertebrae.

BRIEF DESCRIPTION OF THE DRAWINGS

FIG. 4 is a side view of a pseudo arthrosis device.

FIG. 5 is a back view of a pseudo arthrosis device.

FIG. 6 is a cross-sectional view taken substantially along plane 6—6 of FIG. 4.

FIG. 7 is a cross-sectional view taken substantially along plane 7—7 of FIG. 5.

FIG. 8 is a perspective view of a pseudo arthrosis device with a pliable retainer in an enclosure.

Figure 1:
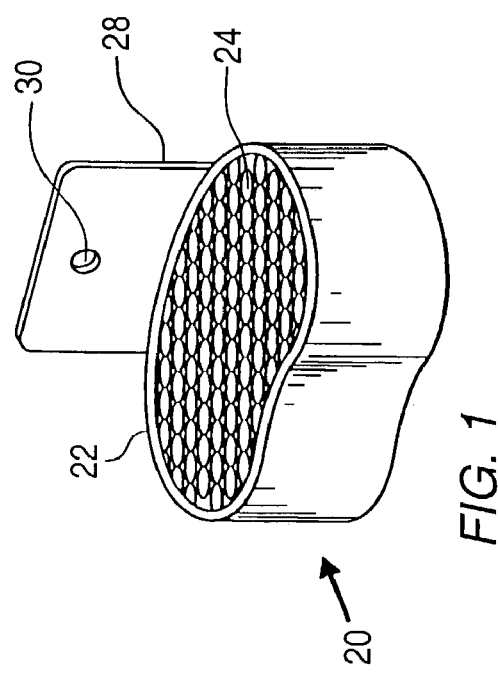
FIG. 1 is a perspective view of a pseudo arthrosis device.

While the invention may be susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF EMBODIMENTS

FIG. 1 depicts pseudo arthrosis device 20 with enclosure 22. Enclosure 22 may be formed from a non-allergenic, biocompatible material. The material may be flexible and/or permeable. The material may include, but is not limited to, synthetic fabrics such as Dacron®, Proline Mesh®, and Goretex®. Enclosure 22 may have a cross-sectional shape corresponding to a cross-sectional shape of an intervertebral space between two adjacent vertebrae in a human spine. Enclosure 22 may be in the form of a tube, a sleeve, an envelope, or other suitable configuration.

As shown in FIG. 1, enclosure 22 may include a plurality of elongated members 24. Elongated members 24 may be compressible and/or flexible. Elongated members 24 may be made of biocompatible materials including, but not limited to, polyethylene, high density polyethylene, ultra high density polyethylene, and various fluorinated polymers. Advantageously, a pseudo arthrosis device including a plurality of elongated members 24 may offer more adaptability, compressibility, and/or flexibility than a device formed of a single piece of substantially the same material.

Longitudinal placement of elongated members 24 in enclosure 22 may allow pseudo arthrosis device 20 to function as a compressible, flexible body. Since the compressibility and flexibility arise from a plurality of elongated members 24, pseudo arthrosis device 20 may provide greater local adaptation to stress between vertebrae than a single deformable piece of material. Flexibility of elongated members 24 and enclosure 22 may allow movement in non-longitudinal directions (e.g., bending and rotation) relative to axes of elongated members 24.

In some embodiments, elongated members 24 may be solid rods. In certain embodiments, elongated members 24 may be hollow tubes. For example, an outer diameter of hollow elongated member 24 may range from about 0.5 mm to about 3.0 mm. An inner diameter of hollow elongated member 24 may range from about 0.25 mm to about 2.0 mm. In an embodiment, elongated member 24 may have a wall thickness of about 1 mm.

Figure 3:
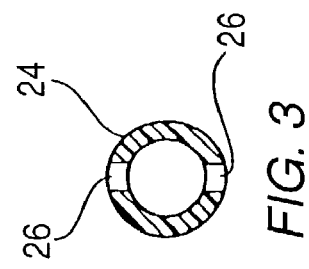
FIG. 3 is a cross-sectional view taken substantially along plane 3—3 of FIG. 2.
Figure 2:
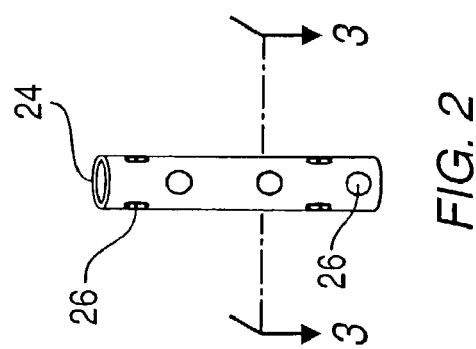
FIG. 2 is a side view of an elongated member.

FIG. 2 depicts hollow elongated member 24 with a plurality of spaced-apart perforations 26. Flexibility of elongated member 24 may be a function of wall thickness of the elongated member and number and size of perforations 26. Perforations 26 may increase flexibility of solid as well as hollow elongated members 24. A length of elongated member 24 may be chosen to achieve desired intervertebral spacing and/or desired flexibility. FIG. 3 depicts a cross-sectional view of hollow elongated member 24 with perforations 26 taken substantially along plane 3—3 of FIG. 2.

As shown in FIG. 1, pseudo arthrosis device 20 may include at least one tab 28. Tab 28 may be of any suitable size, shape, or configuration to couple pseudo arthrosis device 20 to a vertebra. In some embodiments, tab 28 may be an integral part of pseudo arthrosis device 20. In other embodiments, tab 28 may be coupled to enclosure 22. In some embodiments, tab 28 may extend substantially perpendicularly upward from enclosure 22. In other embodiments, tab 28 may extend substantially perpendicularly downward from enclosure 22. In certain embodiments, tab 28 may extend substantially perpendicularly upward and downward from enclosure 22. Alternatively, a first tab 28 may extend substantially perpendicularly upward from enclosure 22 and a second tab 28 may extend substantially perpendicularly downward from enclosure 22. In certain embodiments, enclosure 22 and tab 28 may be made of substantially the same material.

Tab 28 may include at least one opening 30. Opening 30 may be reinforced with a grommet. A grommet used to reinforce opening 30 may be made of titanium or any other durable biocompatible material. In an embodiment, pseudo arthrosis device 20 may be secured to a vertebra by a connector or fastener inserted through opening 30. In certain embodiments, a connector may be a threaded screw. Alternatively, tab 28 may be connected to a vertebra by methods including the use of, but not limited to the use of, sutures, staples, barbs, and/or adhesive.

FIG. 4 depicts a side view of pseudo arthrosis device 20 with enclosure 22 and tab 28. FIG. 5 depicts a back view of pseudo arthrosis device 20 with enclosure 22, tab 28, and openings 30.

FIG. 6 depicts a cross-sectional view of pseudo arthrosis device 20 taken substantially along plane 6—6 of FIG. 4. FIG. 7 depicts a cross-sectional view of pseudo arthrosis device 20 taken substantially along plane 7—7 of FIG. 5. FIGS. 6 and 7 depict a plurality of elongated members 24 placed longitudinally in enclosure 22 with coupled tab 28. In the embodiment shown in FIG. 7, enclosure 22 has top 32 and bottom 34 to promote retention of elongated members 24 in the enclosure. In some embodiments, top 32 and/or bottom 34 may be made of bioabsorbable material (e.g., Surgicel).

In some embodiments, such as the embodiment shown in FIG. 8, pliable retainer 36 may be located transversely in enclosure 22 of pseudo arthrosis device 20. Pliable retainer 36 may have a plurality of spaced-apart holes 38. Elongated members may be positioned securely in holes 38 (e.g., with a friction fit). Elongated members in holes 38 may be retained in an upright packed condition (oriented longitudinally) when pseudo arthrosis device 20 is inserted into a disc space between adjacent vertebrae.

Figure 9:
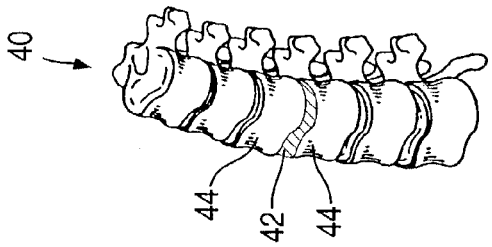
FIG. 9 depicts a portion of a spinal column with a deteriorated disc.
Figure 10:
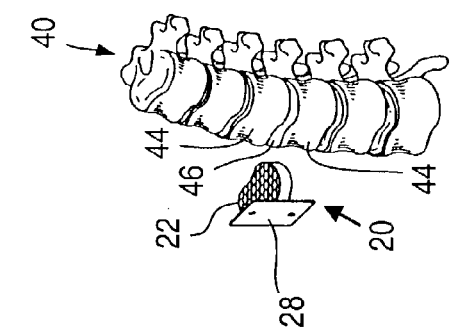
FIG. 10 depicts a pesudo arthrosis device positioned for insertion into a disc space.

FIGS. 9–12 depict a method of implanting a pseudo arthrosis device. FIG. 9 depicts a portion of a spinal column 40 with deteriorated disc 42 between adjacent vertebrae 44. Deteriorated disc 42 may be removed from spinal column 40 to form disc space 46, as shown in FIG. 10.

Figure 11:
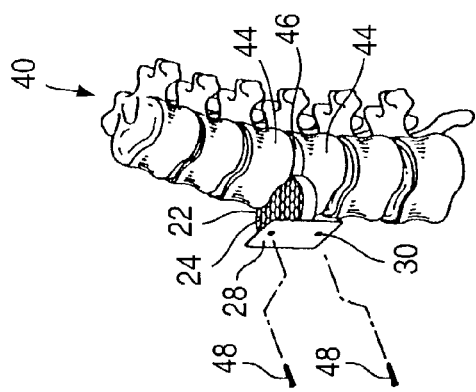
FIG. 11 depicts insertion of a pseudo arthrosis device into a disc space.
Figure 12:
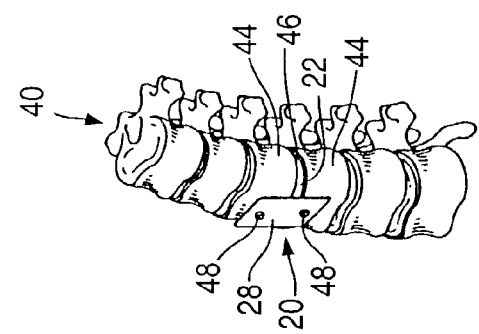
FIG. 12 depicts a pseudo arthrosis device positioned in a disc space.
Figure 13:
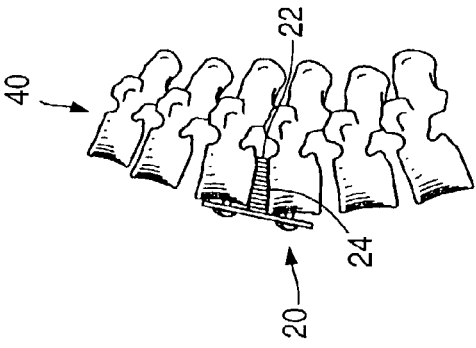
FIG. 13 depicts a portion of a spine showing compression of an implanted pseudo arthrosis device when a patient bends backwards.
Figure 14:
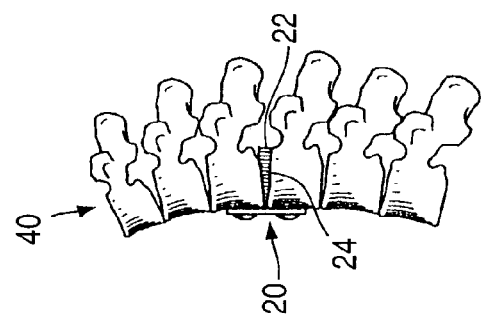
FIG. 14 depicts a portion of a spine showing compression of an implanted pseudo arthrosis device when a patient bends forwards.

FIG. 10 depicts pseudo arthrosis device 20 with enclosure 22 and tab 28 positioned for insertion into disc space 46 between adjacent vertebrae 44. As shown in FIG. 11, elongated members 24 in enclosure 22 are disposed longitudinally between adjacent vertebrae 44 in disc space 46. In an embodiment, tab 28 may be coupled to adjacent vertebrae 44 with connectors 48. Tab 28 may be sized to secure enclosure 22 to adjacent vertebrae 44 with minimal limitation of vertebral movement. FIG. 12 depicts pseudo arthrosis device 20 implanted into spinal column 40. In an embodiment, tab 28 and connectors 48 may secure enclosure 22 of pseudo arthrosis device 20 in disc space 46 between adjacent vertebrae 44.

Figure 15:
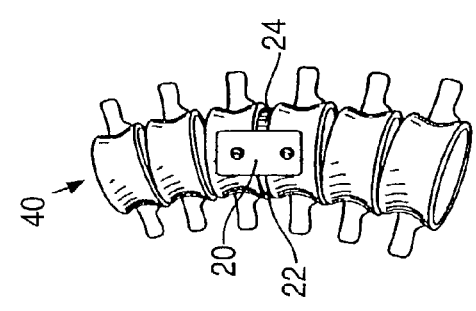
FIG. 15 depicts a portion of a spine showing compression of a pseudo arthrosis device when a patient leans laterally to the right.
Figure 16:
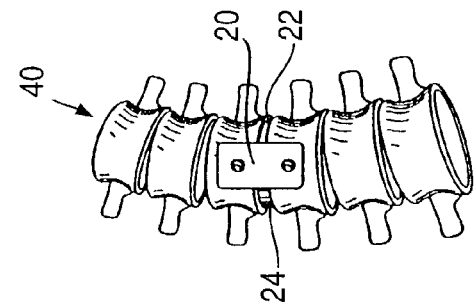
FIG. 16 depicts a portion of a spine showing compression of a pseudo arthrosis device when a patient leans laterally to the left.

FIGS. 13–16 show flexion and compression of elongated members 24 following implantation of pseudo arthrosis device 20 in spinal column 40 of a patient. As the patient bends backwards (FIG. 13) or forwards (FIG. 14), elongated members 24 proximal to the bend of the spine are compressed while the elongated members distal to the bend of the spine are fully extended. FIGS. 15 and 16 depict compression of elongated members 24 when a patient leans laterally right and left, respectively. Compression and extension of elongated members 24 may cushion vertebrae of spinal column 40, thereby simulating natural disc function. In some patients, pseudo arthrosis device 20 may reduce wear and tear on vertebrae of a spinal column and thus relieve spinal pain.

Figure 18:
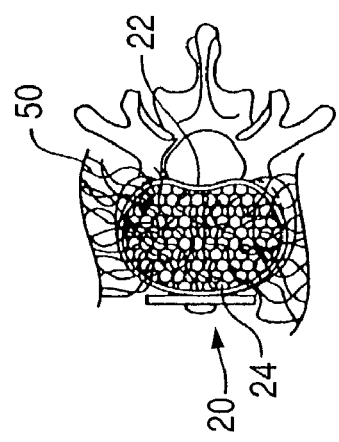
FIG. 18 is a cross-sectional view taken substantially along line 18—18 of FIG. 17 showing fibrous ingrowth.
Figure 17:
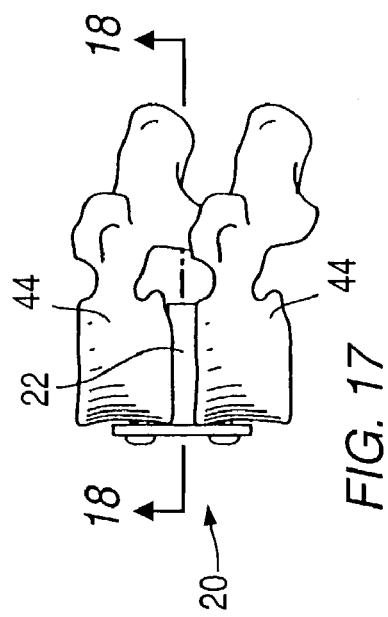
FIG. 17 is an enlarged view showing placement of a pseudo arthrosis device in a disc space.

FIG. 17 depicts pseudo arthrosis device 20 after implantation in a disc space between adjacent vertebrae 44. FIG. 18 depicts a cross-sectional view of pseudo arthrosis device 20 taken substantially along line 18—18 in FIG. 17. As shown in FIG. 18, fibers 50 of a patient may penetrate enclosure 22. Fibers 50 that penetrate enclosure 22 may promote fibrous tissue growth in spaces between elongated members 24. Normal movement of the patient and flexibility of pseudo arthrosis device 20 may inhibit conversion of fibrous tissue growth in enclosure 22 into bone.

Figure 19:
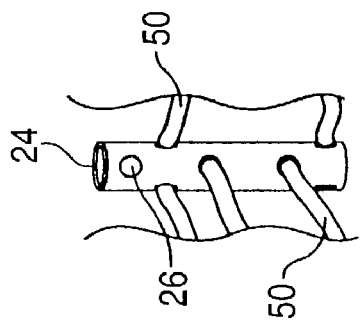
FIG. 19 is an enlarged view of an elongated member showing fibrous ingrowth.

FIG. 19 depicts growth of fibers 50 through perforations 26 in elongated member 24. In an embodiment, fibers 50 may grow longitudinally through hollow elongated member 24. Over time, pseudo arthrosis device 20 may be incorporated into scar tissue formed from fibrous ingrowth of a patient. In certain embodiments, pseudo arthrosis device 20 may advantageously function as a scaffold or matrix to promote natural body repair by fibrous ingrowth.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A pseudo arthrosis device, comprising:
an enclosure formed from a synthetic fabric that is permeable, a plurality of elongated members formed of a biocompatible polymer, wherein at least two of the elongated members are packed together longitudinally in the enclosure wherein the elongated members are in an upright packed condition when the device is inserted into a disc space between two adjacent vertebrae, and wherein the elongated members are in the form of hollow tubes or solid rods, a pliable retainer positioned transversely in the enclosure, wherein the pliable retainer comprises a plurality of spaced-apart holes, and wherein at least one of the plurality of elongated members is positioned in at least one of the plurality of spaced-apart holes, and at least one tab coupled to the enclosure for attaching the pseudo arthrosis device to a vertebrae.

2. The device of claim 1, wherein the enclosure comprises a flexible, permeable material.

3. The device of claim 1, wherein the enclosure comprises a top.

4. The device of claim 1, wherein the enclosure comprises a bottom.

5. The device of claim 1, wherein the enclosure comprises a top and a bottom.

6. The device of claim 1, wherein at least one of the plurality of elongated members comprises a flexible material.

7. The device of claim 1 wherein at least one of the plurality of elongated members comprises a compressible material.

8. The device of claim 1, wherein at least one of the plurality of elongated members comprises a solid elongated member.

9. The device of claim 1, wherein at least one of the plurality of elongated members comprises a hollow elongated member.

10. The device of claim 1, wherein at least one of the plurality of elongated members comprises an outer diameter ranging from about 0.5 mm to about 3.0 mm.

11. The device of claim 1, wherein at least one of the plurality of elongated members comprises a plurality of spaced-apart perforations.

12. The device of claim 1, wherein the at least one tab comprises at least one opening for coupling the device to the vertebra.

13. The device of claim 1, wherein the elongated members are made of a polyethylene.

14. The device of claim 1, wherein the enclosure is in the form of a tube, a sleeve or an envelope.

15. A pseudo arthrosis device, comprising:
an enclosure formed from a synthetic fabric that is permeable;
a plurality of elongated members, wherein at least two of the elongated members are packed together longitudinally in the enclosure, wherein the elongated members are in an upright packed condition when the device is inserted into a disc space between two adjacent vertebrae;
a pliable retainer positioned transversely in the enclosure, wherein the pliable retainer comprises a plurality of spaced-apart holes, and wherein at least one of the plurality of elongated members is positioned in at least one of the plurality of spaced-apart holes; and
wherein at least one of the plurality of elongated members comprises a hollow elongated member.

16. The device of claim 15, wherein at least one of the plurality of elongated members comprises a solid elongated member.

17. The device of claim 15, further comprising at least one tab coupled to the enclosure for attaching the pseudo arthritis device to a vertebra.

18. The device of claim 15, further comprising at least one tab coupled to the enclosure for attaching the pseudo arthrosis device to a vertebra, wherein the at least one tab comprises at least one opening for coupling the device to the vertebra.

19. The device of claim 15, wherein the enclosure comprises a flexible, permeable material.

20. The device of claim 15, wherein the enclosure comprises a top.

21. The device of claim 15, wherein the enclosure comprises a bottom.

22. The device of claim 15, wherein the enclosure comprises a top and a bottom.

23. The device of claim 15, wherein at least one of the plurality of elongated members comprises a flexible material.

24. The device of claim 15, wherein at least one of the plurality of elongated members comprises a compressible material.

25. The device of claim 15, wherein at least one of the plurality of elongated members comprises an outer diameter ranging from about 0.5 mm to about 3.0 mm.

26. The device of claim 15, wherein at least one of the plurality of elongated members comprises a plurality of a spaced-apart perforations.

27. The device of claim 15, wherein the elongated member are made of a polyethylene.

28. The device of claim 15, wherein the enclosure is in the form of a tube, a sleeve or an envelope.

29. A method of supporting adjacent vertebrae in a spinal column, comprising:

inserting a pseudo arthrosis device between the adjacent vertebrae such that a plurality of elongated members formed of a biocompatible polymer in an enclosure of the arthrosis device is positioned longitudinally in a disc space between the adjacent vertebrae, wherein at least two of the elongated members are packed together longitudinally in the enclosure, wherein the elongated members are in an upright packed condition, wherein the elongated members are in the form of hollow tubes or solid rods and wherein the enclosure is formed from a synthetic fabric that is permeable, wherein a pliable retainer is positioned transversely in the enclosure, wherein the pliable retainer comprises a plurality of spaced-apart holes, and wherein one of the plurality of elongated members is positioned in one of the plurality of spaced-apart holes; and attaching a tab coupled to the enclosure of the pseudo arthrosis device to an adjacent vertebra to secure the pseudo arthrosis device in the disc space.

30. The method of claim 29, wherein the tab comprises at least one opening.

31. The method of claim 29, wherein the tab comprises an opening, and wherein attaching the tab to the adjacent vertebra comprises inserting a connector through the opening and fastening the connector to the adjacent vertebra.

32. The method of claim 29, wherein at least one of the plurality of elongated members comprises a flexible material.

33. The method of claim 29, wherein at least one of the plurality of elongated members comprises a compressible material.

34. The method of claim 29, wherein at least one of the plurality of elongated members comprises a hollow tube.

35. The method of claim 29, wherein at least one of the plurality of elongated members comprises a solid rod.

36. The method of claim 29, wherein the elongated members are made of a polyethylene.

37. The method of claim 29, wherein the enclosure is in the form of a tube, a sleeve or an envelope.

* * * * *